US005686409A

United States Patent [19]

McFadden et al.

[11] Patent Number: 5,686,409

[45] Date of Patent: Nov. 11, 1997

[54] ANTIRESTENOSIS PROTEIN

[75] Inventors: D. Grant McFadden; Alexandra Lucas, both of Edmonton, Canada

[73] Assignee: Research Corporation Technologies, Inc., Tucson, Ariz.

[21] Appl. No.: 232,238

[22] PCT Filed: Apr. 8, 1994

[86] PCT No.: PCT/US94/03895

§ 371 Date: May 2, 1994

§ 102(e) Date: May 2, 1994

[87] PCT Pub. No.: WO95/27503

PCT Pub. Date: Oct. 18, 1995

[51] Int. Cl.$^6$ .......................... A61M 31/00; C07K 14/00

[52] U.S. Cl. .......................... 514/12; 604/53; 604/269; 604/265; 604/266

[58] Field of Search .......................... 514/12; 604/53, 604/269, 265, 266

[56] References Cited

U.S. PATENT DOCUMENTS 5,171,217 12/1992 March et al. .......................... 605/53

OTHER PUBLICATIONS

Liu et al., (1993) "A Novel Viral Anti-Inflammatory Protein, SERP-1, Reduces Intimal Hyperplasia in Cholesterol-Fed Rabbits after Balloon Angioplasty" Abstracts from the 66th Scientific Sessions, Georgia World Congress Center, Atlanta, GA and Supplement to *Circulation 88* (4) (2):181 (Abstract No. 0420).

Lucas et al., (1994) "A Unique Viral Anti-Inflammatory Protein, SERP-1, Reduces Intimal Hyperplasia in Cholesterol Fed Rabbits After Angioplasty" *Journal of Cellular Biochemistry* Suppl. 18A:286 (Abstract No. E315).

Upton et al., (1986) "A Novel Member of the Serpin Superfamily is encoded on a Circular Plasmid-like DNA Species Isolated from Tabbit Cells" *FEBS Letters* 207 (1):115-120.

PCT Search Report: PCT/US9403895.

Abst. from 66th Scientific Sessions, Circulation, vol. 88, No. 4(2) Oct., 1993 p. I81, Abst. 0420.

Abst. from J. of Cellular Biochem., vol. 0, No. 18A, 4 Jan., 1994, New York, N.Y. p. 286, Abst. #E315.

H. Vernon Anderson (1993) "Restenosis After Coronary Angioplasty" *Disease-a-Month* vol. XXXIX, No. 9, pp. 613-672, Roger Bone, ed., Mosby, St. Louis, MO.

Steven R. Bailey (1993) Coronary Restenosis After Angioplasty, *J. Intensive Care Medicine*, 6(3):105-114.

Lovquist et al (1993) Pathophysiological Mechanisms For Restenosis Following Coronary Angioplasty: Possible Preventive Alternatives, *J. Internal Medicine* 233:215-226.

Franklin et al. (1993) Pharmacologic Prevention of Restenosis After Coronary Angioplasty: Review of the Randomized Clinical Trials, *Coronary Artery Disease* 4(3)233-242.

Linda R. Gooding (1992) Virus Proteins That Counteract Host Immune Defenses, *Cell* 71:5-7.

Herrman et al. (1993) Pharmacological Approaches to the Prevention of Restenosis Following Angioplasty, The Search for the Holy Grail? (Part I) *Drugs* 46(1):18-52.

Herrman et al. (1993) Pharmacological Approaches to the Prevention of Restenosis Following Angioplasty, The Search for the Holy Grail? (Part II) *Drugs* 46(2):249-262.

Lomas et al. (1993) Inhibition of Plasmin, Urokinase, Tissue Plasminogen Activator, and Cls by Myxoma Virus Serine Proteinase Inhibitor, *J. Biol. Chem.* 268(1)516-521.

Macen et al. (1993) SERPl, A Serine Proteinase Inhibitor Encoded by Myxoma Virus, is a Secreted Glycoprotein that Interferes with Inflammation, *Virology* 195:348-363.

Schwartz et al. (1990) Restenosis After Balloon Angioplasty, A Practical Proliferative Model in Porcine Coronary Arteries, *Circulation* 82:(6)2190-2200.

Simons et al. (1992) Antisense c-myb Oligonucleotides Inhibit Intimal Arterial Smooth Muscle Cell Accumulation In Vivo, *Nature* 359:67-70.

Upton et al. (1990) Myxoma Virus and Malignant Rabbit Fibroma Virus Encode a Serpin-like Protein Important for Virus Virulence, *Virology* 179:618-631.

Upton et al. (1992) Encoding of a Homolog of the IFN-$_y$ Receptor by Myxoma Virus, *Science* 258:1369-1372.

Wanibuchi et al. (1993) Is the Watanabe Heritable Hyperlipidemic Rabbit a Suitable Experimental Model for Percutaneous Transluminal Coronary Angioplasty in Humans? *JACC* 21(6)1490-1496.

*Primary Examiner*—Howard E. Schain
*Assistant Examiner*—P. Lynn Touzeau
*Attorney, Agent, or Firm*—Scully, Scott, Murphy & Presser

[57] ABSTRACT

A method of treating primary and recurrent atheromatous plaque development is provided. The method involves administering a therapeutically effective amount of SERP-1, admixed in a pharmaceutically acceptable carrier to the intimal or lumenal layer of arterial walls. Biologically active SERP-1 analogs are also provided.

24 Claims, 13 Drawing Sheets

Area of Balloon mediated intimal injury

Area of SERP-1 infusion

FIG. 7A

```
 ATGAAGTATCTGGTCCTCGTCTTATGTTTAACGTCGTGCGCGTGTCGAGATATCGGAC
 M  R  Y  L  V  L  V  L  C  L  T  S  C  A  C  R  D  I  G  L

TATGGACGTTCCGATACGTCTACAACGAAAGCGACAACGTCGTGTTCTCACCGTACGGCT
 W  T  F  R  Y  V  Y  N  E  S  D  N  V  V  F  S  P  Y  G  L

TGACCTCCGCGTTGTCCGTGTTACGGATCGCGGCGGGCGGTAACACGAAACGAGAAATAG
 T  S  A  L  S  V  L  R  I  A  A  G  G  N  T  K  R  E  I  D

ACGTCCCCGAATCCGTCGTGGAGGACTCCGACGCCTTTCTCGCGTTACGGGAGTTGTTCG
 V  P  E  S  V  V  E  D  S  D  A  F  L  A  L  R  E  L  F  V

TAGACGCATCCGTTCCGTTACGTCCCGAGTTTACGGCGGAGTTCTCCTCGCGATTCAATA
 D  A  S  V  P  L  R  P  E  F  T  A  E  F  S  S  R  F  N  T

CCTCCGTGCAACGCGTGACGTTTAACTCGGAGAACGTCAAAGACGTCATTAACTCGTACG
 S  V  Q  R  V  T  F  N  S  E  N  V  K  D  V  I  N  S  Y  V

TTAAGGATAAGACGGGAGGAGACGTCCCACGCGTATTGGACGCCTCCCTAGACCGAGATA
 K  D  K  T  G  G  D  V  P  R  V  L  D  A  S  L  D  R  D  T

CTAAAATGCTGCTATTGAGCTCCGTTCGTATGAAGACGAGCTGGAGACACGTATTCGACC
 K  M  L  L  L  S  S  V  R  M  K  T  S  W  R  H  V  F  D  P

CTTCGTTCACGACGGATCAACCTTTTTATTCCGGAAACGTCACATACAAGGTACGTATGA
 S  F  T  T  D  Q  P  F  Y  S  G  N  V  T  Y  K  V  R  M  M

TGAATAAAATAGATACGTTGAAAACGGAGACGTTTACGCTTAGAAACGTGGGATACTCCG
 N  K  I  D  T  L  K  T  E  T  F  T  L  R  N  V  G  Y  S  V
```

FIG. 7B

```
TAACGGAACTGCCGTATAAACGGCGTCAAACGGCCATGTTGCTCGTCGTTCCGGACGACT
  T  E  L  P  Y  K  R  R  Q  T  A  M  L  L  V  V  P  D  D  L

TGGGAGAGATCGTGCGGGCCCTCGATCTTTCTCTAGTACGCTTCTGGATACGCAACATGA
  G  E  I  V  R  A  L  D  L  S  L  V  R  F  W  I  R  N  M  R

GGAAAGACGTGTGTCAGGTGGTAATGCCCAAGTTCTCCGTCGAATCGGTCCTGGATCTGA
  K  D  V  C  Q  V  V  M  P  K  F  S  V  E  S  V  L  D  L  R

GGGACGCCCTCCAGAGACTGGGGGTGCGAGACGCGTTCGATCCATCCCGGGCGGACTTCG
  D  A  L  Q  R  L  G  V  R  D  A  F  D  P  S  R  A  D  F  G

GTCAGGCGTCCCCGTCGAACGATCTATACGTCACGAAGGTGTTACAGACGTCCAAGATAG
  Q  A  S  P  S  N  D  L  Y  V  T  K  V  L  Q  T  S  K  I  E

AGGCGGACGAACGGGGAACGACGGCGTCGAGCGACACAGCCATCACCCTCATCCCCAGGA
  A  D  E  R  G  T  T  A  S  S  D  T  A  I  T  L  I  P  R  N

ACGCCCTCACGGCGATCGTGGCGAACAAACCGTTTATGTTTCTCATCTATCACAAGCCTA
  A  L  T  A  I  V  A  N  K  P  F  M  F  L  I  Y  H  K  P  T

CAACGACCGTGTTGTTTATGGGAACGATAACAAAGGGTGAAAAAGTAATATACGATACGG
  T  T  V  L  F  M  G  T  I  T  K  G  E  K  V  I  Y  D  T  E

AGGGTCGAGATGATGTCGTATCCTCTGTATAAACTCTTTTTGAAGGGTAAACTATGCGAC
  G  R  D  D  V  V  S  S  V  *
```

ANTIRESTENOSIS PROTEIN

BACKGROUND OF THE INVENTION

The present invention relates to use of a viral protein, SERP-1, its analogs and biologically active fragments in the prevention of vascular intimal hyperplasia and restenosis following arterial recanalization intervention procedures. The present invention also contemplates the use of SERP-1 in the prevention of primary atheromatous plaque formation.

Cellular proliferation and connective tissue deposition associated with atherosclerotic plaque growth produce arterial occlusion, heart attack, stroke, and peripheral occlusion. Recurrence of atherosclerotic lesions (restenosis) occurs after all known interventional procedures designed to open occluded arteries (Jaser and balloon angioplasty, atherectomy, and stent implantation) and remains a significant medical problem. Restenosis is detected in 20–50% of cases within six months, irrespective of the interventional device chosen and 50% of vein grafts occlude within ten years after surgery. Detre et al., 1989 Am J Cardiol 80:421–428; Topol et al., 1993 NEJM 329:221–227; Schatz et al., 1991 JACC 17:155B–159B (abstr).; Ellis et al., 1992 DWM JACC 19:275–277. Restenosis, which usually occurs in the two week to six month post operative period is distinguished from abrupt reclosure of a blood vessel (vasospasm) which occurs immediately after surgery.

The precise trigger for recurrent atherosclerosis is still unknown, but local arterial damage induced during interventional treatment has been demonstrated to produce focal areas of inflammation. At sites of endothelial injury and subsequent restenosis, the inflammatory response becomes over-expressed resulting in intimal cellular proliferation and overly exuberant tissue growth. Dzau et al., 1993 Circulation 87:705–719; Ross, R. 1993 Nature 362:801–809; Fuster et al., 1992 NEJM 326:242–250, 310–318; Marx J., 1990 Science 248:1491–1493; Blanckenhorn et al., 1989 Circulation 79:1–7; Schwartz et al., 1992 JACC 20:1284–1293; Libby et al., 1992 J Cell Biochem 16A:2 (abstract); Westlin et al., 1991 Am J Pathol 142:117–125; Faruqi et al., 1993 Br Heart J 69:S19–S29; Hansson GK, 1993 Br Heart J 69:S38–S41; Ellis et al., DWM JACC 19:275–277; Schwartz et al., 1992 JACC 19:267–274. Inflammatory reactions associated with local intimal injury are also believed to be responsible for the initiation of de novo (primary) plaque development in many cases.

The stimulus for smooth muscle cell or monocyte proliferation, which is believed to initiate atheroma development (Schatz et al., 1991JACC 17:155B–159B(abstr); Ross,R. 1993 Nature 362: 801–809.) has been variously attributed to trauma (Helin et al., 1971 Atherosclerosis 13:319–331; Watanabe, Y. 1980 Aterosclerosis 13:319–331), hyperlipidemia (Wantanabe, Y. 1980; Goldstein et al., 1979 Nature 279:679–685), auto-immune reactions (See eg., Lopes-Virella et al., 1985 G. Clin. Immunol. Path. 37:377–386; Nitkin et al., 1985 JACC f: 243–245) and viral or autocrine induction of benign smooth muscle tumors (Minick et al., 1973 GE Am. J. Pathol 73:265–325; Benditt et al., 1973 PNAS 70: 1753–1756; Simons et al., 1992 Nature 359:67–70). Endothelial damage secondary to any of the interventional devices currently used to re-open occluded arteries (laser, balloon, atherectomy, or stent) generally initiates a local inflammatory reaction. This endothelial damage and the associated inflammatory response is believed to be the underlying source for the stimulus to cellular proliferation and restenosis. After localized intimal damage has occurred, circulating cells such as platelets, monocytes, and T cells adhere to the area of injury and become activated (Pruzanski et al., 1991 Immunol Today 12:143–146; Poston et al., 1992 Am. J. Pathol 140:665–673). Thus, the act of mechanically opening a stenosed artery produces a sequence of events involving the inflammatory and immune systems that frequently results in regrowth of plaque at the site of injury, i.e., restenosis. Similar processes are believed to effect the production of cellular proliferation in other inflammatory based disorders such uretal or urethral stricture and inflammatory diseases of the bladder.

Other parameters involved in the initial arterial injury that can produce atherosclerotic plaque and affect progression into an occluded artery (viral, autoimmune, or hyperlipidemic mechanisms) may be related to the underlying tendency for plaque recurrence at the site of interventional therapy. Many of the diverse cellular and molecular pathways involved in the localized response to injury are believed to play a role in initiating the exacerbated wound/repair response that leads to restenosis.

Why plaque growth accelerates with eventual rupture, hemorrhage, and/or fissure is not completely understood; nor have the exact mechanisms involved in the recurrence of plaque after interventional therapy been well delineated. It is known, however, that platelet activation results in the release of inflammatory proteins and growth factors (Ross R., 1993 Nature 362: 801–809, Fuster et al., 1992 NEJM 326:801–809; Ambrose et al., 1988 JACC 12:56–62, Ambrose et al., 1986 JACC 7: 472–478). These inflammatory proteins in turn act to attract monocytic cells, T cells, and smooth muscle cells which migrate into the intimal layer of the artery at the site of injury. It has also been demonstrated that platelet derived growth factor (PDGF) is present in plaque specimens derived from obstructed human carotid artery (Lebby et al., 1988 NEJM 318:1493–497). In a recent report, Nude mice treated with PDGF after arterial injury had accelerated plaque development. This suggests that stimulation of target cells expressing the PDGF receptor is one component of the hyperplasia associated with restenosis. Inhibition of cMyb and PDGF has been reported to decrease cellular proliferation at sites of arterial injury (Simons et al., 1992 Nature 359:67–70.). In addition, other growth factors such as TGF beta have been associated with cellular proliferation related to endothelial injury (Ross R., 1993 Nature 362:801–809). Numerous cytokines (signaling molecules involved in cellular messages in the inflammatory and immune system) have been implicated in plaque development; examples include Tumor Necrosis Factor (TNF) and gamma interferon (gIF), Interleukins 1 and 6, and a variety of cellular adhesion molecules (Ross et al., 1993; Fuster et al., 1992, Libby et al., Cell Biochem 16A:2 (abstr)).

Proteins having anti-immune properties which play a role in immunosuppression are produced by some of the large DNA viruses. (See e.g., Gooding L.R.,1992 Cell 71: 5–7, McFadden, G., Human Cytokines: Their Role in Health and Disease, eds. BB Agarwall and RK Purl Blackwell Press [1993 , in press]). For example, members of Leporipoxvirus encode at least four such proteins with anti-immune properties: (1) secreted homologues for the cellular receptors for Tumor Necrosis Factor (TNF) and gamma Interferon, (2) a receptor like protein, M11L, of unknown function, and (3) a serine protease inhibitor, SERP-1 that has demonstrated ability to interfere with the host inflammatory response to infection. (See e.g., Gooding L. R., 1992 Cell 71:5–7, McFadden, G., Enc. of Virology, RG Webster and A. Granhoff, WB Saunders Co., [1993, in press]; Grahem et al., 1992 Virol. 191:112–124.) The success of these strategies is demonstrated by the fact that one such member, Myxoma virus, produces widespread, malignant infections in rabbits that are almost invariably lethal.

Malignant rabbit fibroma virus (MRV) and Myxoma virus (MYX) produce a 55 kDa serine protease inhibitor (SERP-1) which is involved in the virulence of MYX and MRV infections. The SERP-1 protein exhibits significant amino acid similarity to the serpin family of serine proteinase inhibitors. The inhibitory specificity of the serine proteinase inhibitors is mainly defined by the residues present at the $P_1$–$P_1$' position of the reactive site. See Lomas et al., 1993 J. Biol. Chem., 268(1):516–521. The amino acids present in the P1–P1' position act as a psuedosubstrate for the cognate proteinase. The cognate proteinase binds to the serpin in a 1:1 ratio and is inactivated upon complex formation. Id.

It has recently been shown that myxoma virus SERP-1 binds to and inhibits the proteolytic activities of the human proteinases plasmin, urokinase, tissue plasminogen activator, and Cls (Lomas et al. 1993). Both the nucleotide sequence and amino acid sequence of SERP-1 is known. See Upton et al., 1990 Virology 179:618–631. The translated SERP-1ORF is identical in both MRV and MYX. Id.

Despite more than a decade of clinical experience and research in the field of restenosis after percutaneous transluminal coronary angioplasty (PCTA), no major breakthroughs in pharmacological interventions have occurred. Herrman et al, 1993 Drugs 46(2):149–262. For example, use of antiplatelet agents such as aspirin, dipyridamole and ticlopidine have not resulted in reduction in restenosis rates. Anderson, Kitazume et al., 1988 Circulation 78(II):633. Anticoagulants, such as heparin and coumadin have also been shown ineffective in reducing restenosis. Clinical trials with fish oils (high in ω fatty acids) as dietary supplements have yielded encouraging but not dramatic results. Use of prostanoid products such as thromboxane, prostacyclin and serotonin have not proved effective. Nor has the use of antiaggregatory, antivasospastic prostacyclin-type compounds or inhibitors of thromboxanes resulted in reduced rates of restenosis. Similarly, two large clinical trials of angiotensin-converting enzyme inhibitors failed to demonstrate any benefit in reducing restenosis. Calcium-channel antagonists, β-adrenergic receptor antagonists, lipid-lowering agents, and the antimitotic agent colchicine have also proved ineffective.

Restenosis following arterial recannalization intervention procedures remains a serious clinical problem. As noted, available pharmaceutical products have not proved effective in reducing recurrent atheromatous plaque development. There is a need therefore, for a clinical agent which is effective in preventing primary and recurrent atherosclerosis.

SUMMARY OF THE INVENTION

In accordance with the present invention, it has been surprisingly discovered that the viral protein SERP-1, its analogs and biologically active fragments thereof prevents, inhibits and/or ameliorates atherosclerosis including restenosis and de novo plaque development.

The present invention provides a method for treatment including the inhibition and amelioration of atherosclerosis. In accordance with the present invention, the viral protein SERP-1, SERP-1 analogs and biologically active fragments thereof, are administered at the site of prior damage to the intimal and medial layers of the arterial wall. In accordance with the present invention therefore, SERP-1, its analogs and biologically active fragments are employed in a method for the treatment, inhibition and prevention of restenosis.

The present invention is also directed to the treatment, prevention and inhibition of primary (de novo) plaque development. In this embodiment of the invention, SERP-1, SERP-1 analogs or biologically active fragments thereof, are administered to the arterial walls in areas which may or may not yet exhibit atheromatous plaque development.

In accordance with the present invention, a method for treating ureteral or urethral stricture and chronic. inflammatory disease of the bladder caused by various pathological conditions is provided through the administration of SERP-1, its analogs and biologically active fragments to the lumenal layers of the urethra and/or ureters.

In another embodiment of the present invention, pharmaceutical compositions are provided which include SERP-1, its analogs or biologically active fragments thereof admixed with a pharmaceutically acceptable carrier.

In a further embodiment, the present invention is directed to an article of manufacture comprising packaging material and a pharmaceutical agent contained within the packaging material and wherein the pharmaceutical agent is effective for treating atheromatous plaque development and wherein the packaging material comprises a label which indicates that the pharmaceutical agent can be used for treating atheromatous plaque development.

These and other objects of the invention are accomplished by the administration of SERP-1, its analogs and biologically active fragments thereof in amounts sufficient to affect the desired therapeutic effect.

BRIEF DESCRIPTION OF THE DRAWINGS

FIG. 7 depicts the nucleotide sequence of the Myxoma virus (MYX) SERP-1 open reading frame (ORF). (SEQ ID NO:1).

DETAILED DESCRIPTION OF THE INVENTION

Figure 1:
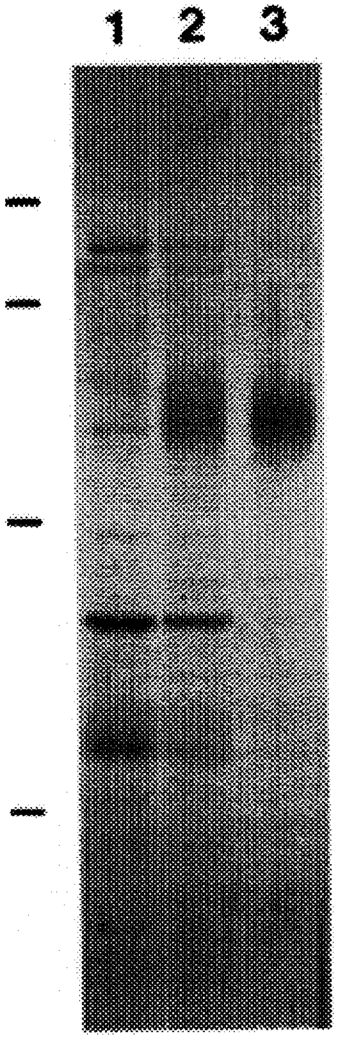
FIG. 1 is a photograph showing electrophoretic migration patterns of the SERP-1 protein and vaccinia vector control in a silver stained SDS polyacrylamide gel. Lane 1 shows the electrophoretic pattern of Mono-Q purified VV-601 (control vector). Lane 2 shows the electrophoretic pattern of the Mono-Q purified SERP-1 protein from VV-S1. Lane 3 depicts the electrophoretic pattern of the SERP-1 protein further purified to homogeneity by Superdex 75. "Semi-purified" SERP-1 refers to the sample in Lane 2. Experiments involving administration of semi-purified SERP-1 used vaccinia vector proteins purified in a similar manner [Lane 1] as a control. "Purified" SERP-1 refers to the preparation in Lane 3. Experiments involving administration of purified SERP-1 were performed with saline as the control.

In accordance with the present invention, it has been surprisingly discovered that the protein SERP-1, a serine protease inhibitor produced by malignant rabbit fibroma virus (MRV) and myxoma virus (MYX), its analogs and biologically active fragments thereof, inhibit, prevents and ameliorates the physiologically effects of primary and recurrent atheromatous plaque development and therefore is efficacious in the treatment of de novo plaque development and recurrent atheromatous plaque development (restenosis).

More specifically, in accordance with the present invention, a therapeutically effective amount of SERP-1, SERP-1 analogs or biologically active fragments thereof, are administered during or immediately following an arterial recannalization intervention procedure at the site of intimal injury in order to prevent subsequent restenosis, common in patients after such procedures. In this embodiment of the invention, the SERP-1, SERP-1 analog or biologically active fragment is delivered during or after a recannalization intervention procedure (e.g., laser and balloon angioplasty, atherectomy, vein graft, stent Implantation, coronary bypass surgery) in a manner consistent with conventional methodologies associated with such recannalization intervention procedures. The SERP-1, SERP-1 analog or biologically active fragment thereof may be delivered to the site of arterial intimal injury via a perforated catheter, e.g., a Wolinsky catheter in an amount sufficient to achieve the desired treatment.

In another aspect of the invention, the SERP-1, SERP-1 analog or biologically active fragment thereof is applied directly onto an atheromatous site which has not been subject to a preceding recannalization procedure. In this embodiment, the SERP-1 protein may be delivered via a weeping balloon type catheter, e.g., Cordis. Other application methods which allow the SERP-1 protein to be slowly leaked onto the atheromatous site can be used. As used herein, "atheromatous site" refers to a site in an arterial blood vessel which is affected with or is of the nature of atheroma.

In another embodiment of the invention, a therapeutically effective dose of SERP-1, SERP-1 analog or biologically active fragment thereof, is administered to arterial walls which have not undergone or are not undergoing recannalization and which are not yet displaying signs of atheromatous plaque development. In this aspect of the invention, the administration of SERP-1, analogs or fragments is for purposes of treating, i.e., preventing or inhibiting primary (de novo) plaque development. The delivery system to be used in this embodiment of the invention may be peripheral intravenous infusion, preferably in the hand. Intra-arterial infusion may also be employed. Alternatively, the SERP-1 protein, analogs or fragments may be applied directly to areas of the arterial wall endothelium via a slow leaking catheter.

As a means of treating e.g., preventing the recurrence of urinary tract narrowing, SERP-1 protein, analogs or fragments may be delivered to the lumenal layers of the ureters and/or urethra by any catheter specific for urinary tract openings. For example, both urethral and/or uretal inflammatory stricture and chronic inflammatory diseases of the bladder may be benefitted by SERP-1 therapy.

In accordance with the present invention, the SERP-1 protein, SERP-1 analog or biologically active fragment thereof, is first isolated and purified so that contaminants are removed. In a preferred method of producing the SERP-1 protein, analog or biologically active fragment of the present invention, a deoxyribonucleic acid (DNA) molecule or segment that defines coding sequence for, i.e., is capable of expressing a SERP-1, SERP-1 analog, or biologically active fragment thereof is used.

Myxoma virus can be obtained from the American Type Culture Collection (ATCC), Accession No. VR-115 DNA can be extracted from the myxoma virus by methods well known in the art. The entire SERP-10RF or fragment thereof can be amplified by well known methods such as the polymerase chain reaction (PCR). The SERP-1 nucleotide and amino acid sequence is published (Upton et al., 1990 Virology 179:618–631) and is also shown in FIG. 7. In this way the entire SERP- 1 ORF or a part thereof is obtained.

A DNA molecule that includes a DNA sequence encoding the subject protein can also be prepared by operatively linking appropriate restriction fragments from various plasmids which are described elsewhere. See e.q., Upton, et al., 1990 virology 179:618–631; Macen et al., 1993 Virology 195:348–363. Also contemplated by the present Invention are ribonucleic acid (RNA) equivalents of the above described molecules.

Thus the SERP-1, SERP-1 analog or biologically active fragment thereof is produced by a recombinant DNA molecule which includes a vector operatively linked, for replication and/or expression to coding sequence for the subject SERP-1 protein. As used herein, the term "vector" refers to a DNA molecule capable of autonomous replication in a cell and to which another DNA segment can be operatively linked so as to bring about replication of the attached segment. Vectors capable of directing the expression of a genes delivered by a subject DNA segment are referred to as "expression vectors".

One method of producing the subject protein of the present invention is by a vector comprising a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, an expression vector includes a procaryotic promoter capable of directing the expression (transcription and translation) of the subject SERP-1 protein, SERP-1 analog or biologically active fragment thereof. Promoter sequences compatible with bacterial hosts are typically provided in plasmid vectors containing convenient restriction sites for insertion of a DNA segment coding for the subject SERP-1 protein, analog, or biologically active fragment thereof.

Preferred expression vectors for the production of SERP-1, SERP-1 analog or biologically active fragment thereof are compatible with eucaryotic cells, and preferably compatible with mammalian cells. Expression of the SERP-1, SERP-1 analog or biologically active fragment thereof in eucaryotic cells is preferred since such cells are able to glycosylate the SERP-1 protein. Eucaryotic cell expression vectors are well known in the art and are available from several commercial sources. Typically, such vectors comprise convenient sites for insertion of a desired DNA segment. Examples of commercially available expression vectors with convenient restriction sites re pSVL, and pKSV-10 (Pharmacia), pBPV-1pML2d (IBI) and pTDT1 (ATCC Accession No. 31255).

The expression vectors compatible with eucaryotic cells and used to construct SERP-1 expression vectors for the production of SERP-1 protein can include a selection marker that is effective in a eucaryotic cell, preferable a drug resistance selection marker. An example of a drug resistance marker is neomycin resistance, obtained through expression of the neomycin phosphotransferase gene.

Preferred eucaryotic host cells include yeast and mammalian cells, preferably vertebrate cells such as those from mouse, rat, monkey, or human fibroblastic cell line. Examples of eucaryotic host cells include Chinese hamster ovary (CHO) cells available from ATCC as CCL61 and NIH Swiss mouse embryo cells NIH/3T3 available from the ATCC as CRL 1658. Transformation of appropriate cell hosts with a recombinant DNA molecule of the present invention is accomplished by well known methods that typically depend on the type of vector used. Transformation methods of procaryotic cells are described in Cohen et al., Proc. Natl. Acad. Sci. USA, 69:2110 (1972). Transformation of vertebrate cells are described in Sambrook et al., 1989 Molecular Cloning: A Laboratory Manual, Cold Spring Harbor Laboratories, Cold Spring Harbor, N.Y.

Successfully transformed cells, i.e., cells which contain a recombinant DNA molecule coding for SERP-1, SERP-1 analog or biologically active fragment thereof can be identified by well known techniques. For example, cells resulting from the introduction of rDNA vectors containing coding sequence for SERP-1, SERP-1 analog, or biologically active fragment thereof can be cloned and amplified to produce monoclonal colonies. Cells from those colonies can be harvested, lysed and their DNA content analyzed for the present of SERP-1DNA using a method such as that described in Southern, J. Mol. Biol., 98–503 (1975) or Brent et al., Biotech., 3:208 (1985).

Besides directly assaying for the presence of SERP-1DNA, successful transformants can be confirmed by well known immunological methods when the rDNA is capable of directing the expression of the subject protein. Cells successfully transformed with an expression vector comprised of coding sequence for SERP-1 produce SERP-1, SERP-1 analog or biologically active fragment thereof. Samples of cells suspected of being transformed are harvested and assayed for the presence of SERP-1 antigenicity using anti-SERP-1 antibodies.

In one embodiment of the invention, BV12-10 a, an M13 clone used in sequencing the myxoma virus BamHI U3 fragment (Upton et al., 1990 Virology 179:618–631) which contains the intact SERP-1 ORF (SEQ ID NO:1) is grown in *E. coli.* (see FIG. 7). The procedures and methodologies employed in the Upton et al. reference are herein incorporated by reference. CJ236 (dut[31] ung⁻; Kunkel et al., 1987 Methods Enzymology, 154:367–382). Oligonucleotide directed mutagenesis is performed as described (Kunkel et al., 1987) in order to insert a BamHI site directly 5' to the SERP-1 initiation codon (GGATCCATG). The resultant phage is propagated in *E. coli.* JM103. A 1301-bp BamHI/HindIII fragment from this phage, containing the intact SERP-1 ORF is subcloned into pMTL22 (Chambers et al., 1988 Gene 68:139–149). A 1344-bp BamHI/BglI fragment is then ligated into the BamHI site of the vaccinia expression plasmid pMJ601 (Davidson et al., 1990 Nucleic Acids Res 18: 4285–4286) allowing SERP-1 to be inserted into the TK gene of vaccinia virus under the control of a strong, synthetic late promoter. Recombinant vaccinia vires (strain WR) is selected on TK-H143 cells in the presence of 25 μg/mL BUdR and plaque purified. Expression of the SERP-1 protein from the recombinant virus (designated VV-S1) is confirmed by immunoblotting using anti-SERP-1 antiserum. Control virus (not containing the SERP-1 ORF) is prepared by generating TK-recombinants of vaccinia WR using the parental pMHJ601 plasmid.

SERP-1 produced from VV-S1 is harvested from the supernatants of monkey BGMK cells twenty four hours after infection with virus at a multiplicity of infection of 1 pfu per cell as described. (Macen et al., 1993 Virology 195:348–363.) The procedures and methodologies employed in the Macen et al. paper are herein incorporated by reference.

In order to collect and purify the secreted SERP-1 glycoprotein produced in VV-S1, the growth medium containing the secreted viral proteins is collected, clarified by centrifugation and dialyzed against 25 mM Tris pH 8.0 and protein may be concentrated, for example with an Amicon Centriprep-10 apparatus. The dialyzed samples are then loaded onto a MonoQ column (Pharmacia) and protein is eluted using a linear salt gradient (0–300 mM NaCl). SERP-1 protein purified in this fashion is semi-purified. Preferably, the SERP-1 protein is then further purified by Superdex-75 column chromatography. SERP-1 protein further purified in this fashion is considered to be more highly purified and exhibits a higher biological activity.

SERP-1 containing fractions may be analyzed by sodium dodecyl sulfate polyacrylamide gel electrophoresis (SDS-PAGE). Total protein concentrations can be determined by well known methods such as Bradford assay. Protein concentrations may also be adjusted and determined by densitometric scans of silver stained gels or Western blotting using bacterially expressed SERP-1 protein as control standards.(20 pre). The control vaccinia vector lacking the SERP-1 ORF can also be harvested and purified from the BGMK cell supernatant in an identical matter.

After purification to a semi-pure or preferably to the more highly purified state, SERP-1 may then be admixed with sterile water and saline or other pharmaceutically acceptable carrier to a concentration in the range of between 3 pg/ml and 30 μg/ml and preferably between 3 pg/ml and 300 ng/ml. Alternatively, the SERP-1, SERP-1 analog, or biologically active fragment thereof, may be stored as a lyophilized powder, or frozen, and then later solubilized in sterile water or saline or other pharmaceutically acceptable carrier to the above delineated concentrations.

The SERP-1 of the present invention may be administered to a human patient preferably as a pharmaceutical composition in a therapeutically effective amount. The pharmaceutical compositions of the present invention contain a therapeutically effective dose of the SERP-1 protein, homologs or analogs thereof or else contain a biologically active fragment of the SERP-1 protein, homologs or analogs thereof together with a pharmaceutically acceptable carrier. The term "therapeutically effective amount" means the dose needed to effectively treat primary or recurrent atheromatous plaque development. For purposes of the present invention, the terms "treat" or "treatment" include preventing, inhibiting, reducing the occurrence of and/or amelioratinf the physiological effects of the condition treated.

As used herein, "analogs" is meant to include substitutions or alterations in the amino acid sequence of the SERP-1 protein, which substitutions or alterations (e.g., additions and deletions) do not abolish the anti-atheroma properties of the protein when administered to the outside surfaces or intimal surfaces of the arterial wall. For purposes of the present invention, the term "analog" includes amino acid insertional derivatives of SERP-1 such as amino and/or carboxyl terminal fusions as well as intra-sequence insertions of single or multiple amino acids. Insertional amino acid sequence variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue in the sequence has been removed and a different residue inserted in its place. Where the protein is derivatized by amino acid substitution, amino acids are generally replaced by other amino acids having similar physical chemical properties such as hydrophobicity, hydrophilicity, electronegativity, bulky side chains and the like.

As used herein, the term "analogs" also encompasses homologs of SERP-1, i.e., corresponding amino acid sequences derived from other SERP-1 proteins and having the same or substantially the same anti-atheroma properties.

SERP-1 amino acid variants may be readily made using peptide synthetic techniques well known in the art such as solid phase peptide synthesis (Merrifield synthesis) and the like or by recombinant DNA techniques well known in the art. Techniques for making substitution mutations at predetermined sites in DNA include for example M13 mutagenesis. Manipulation of DNA sequences to produce substitutional, insertional, or deletional variants are conveniently described elsewhere such as Sambrook et al., 1989 Molecular Cloning: A Laboratory Manual, Cold Spring Harbor Laboratories, Cold Spring Harbor, N.Y.

For purposes of the present invention, analogs of SERP-1 also include single or multiple substitutions, deletions and/or additions of any component(s) naturally or artificially associated with the SERP-1 such as carbohydrate, lipid and/or other proteinaceous moieties. All such molecules are encompassed by the term SERP-1 analogs.

In one embodiment of the invention, in order to increase the specific activity of the prepared SERP-1 protein, the cysteine residue at position 244 may be substituted with another amino acid residue, for example alanine. Such a substitution causes the SERP-1 protein to be more biologically active since $Cys_{244}$ is the predicted position for SERP-1 dimer formation through disulfide bridges. Because $Cys^{244}$ lies very close to the reactive center of the SERP-1 protein, SERP-1 dimmers are thought to have a disturbed and obfuscated reactive center thereby rendering them biologically inactive. Lomas et al., 1993 J. Biol. Chem. 268 (1): 516–521. A mutation at position 244 prevents the formation of SERP-1 dimmers in the production of SERP-1 through recombinant DNA means. A decrease in the presence of SERP-1 dimmers in a preparative sample is useful since the specific activity of the isolated protein will be increased and thus less protein will be needed in a pharmaceutical preparation.

The inhibitory activity of serpins is believed to revolve around the slow dissociation of the serpin from the serine protease after cleavage of the serpin between the P1 and P1' residues in the active region. Upton et al., 1990 Virology 179:618–631. The amino acid sequence Arg/Asp has recently been located at the predicted SERP-1P1-P1' site (amino acid residues 319 and 320) and is the predicted site for cleavage by serine proteases. Substitutions of either or both of these two amino acids produces SERP-1 analogs of varying biological activities useful in the practice of the present invention.

The formulation of pharmaceutical compositions is generally known in the art and reference can conveniently be made to Remington's Pharmaceutical Sciences, 17th ed., Mack Publishing Co., Easton, Pa. Formulation of the SERP-1 protein, analogs, or fragments thereof for use in the present invention must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms of SERP-1 suitable for infusion include sterile aqueous solutions or dispersions and sterile powders for the extemporaneous preparation of sterile injectable solutions or dispersion. In all cases, the form must be sterile and must be fluid to the extent that easy syringability exists. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils. Sterilization can be accomplished by any art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The subject SERP-1 protein or analogs and fragments thereof, are thus compounded for convenient and effective administration in pharmaceutically effective amounts with a suitable pharmaceutically acceptable carrier in a therapeutically effective dose.

As used herein, the term "pharmaceutically acceptable carrier and/or diluent" includes any and all solvents, dispersion media, antibacterial and antifungal agents, isotonic and absorption delaying agents and the like which are not incompatible with the active ingredients (SERP-1, SERP-1 analogs and fragments thereof). The use of such media and agents for pharmaceutical active substances is well known in the art. Supplementary active ingredients may also be incorporated into the compositions and used in the methods of the present invention.

The precise therapeutically effective amount of SERP-1 protein, analog or fragment thereof to be used in the methods of this invention applied to humans cannot be stated due to individual differences in age, weight, extent of atheromatous plaque development and condition of the patient. However, it can generally be stated that the SERP-1 pharmaceutical preparation of the present invention should be preferably administered in an amount of at least about 30 pg per infusion dose, more preferably in an amount up to about 300 μg per dose.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly depend on (a) the unique characteristics of the active material (e.g., SERP-1 protein, SERP-1 analogs, or fragments thereof), (b) the limitations inherent in the art of compounding such an active material for the treatment of atheromatous plaque development as herein disclosed in detail.

The principal active ingredient is compounded for convenient and effective administration in effective amounts with a suitable pharmaceutically acceptable carrier in dosage unit form as hereinabove disclosed. A unit dosage form can, for example, contain the principal active compound in amounts ranging from 0.5 μg to about 200 mg. In the case of compositions containing supplementary active ingredients, the dosages are determined by reference to the usual dose and manner of administration of the ingredients.

Packaging material used to contain the SERP-1 active ingredient can comprise glass, plastic, metal or any other suitable inert material so long as the packaging material does not chemically react with any of the ingredients contained therein.

The SERP-1 protein, analogs or fragments thereof may be administered in a manner compatible with the dosage formulation and in such amount as will be therapeutically effective.

The invention is further illustrated by the following specific examples which are not intended in any way to limit the scope of the invention.

EXAMPLE 1

Purification of Myxoma SERP-1 Protein from Vaccinia Vector

The vaccinia vector (VV-S1) that over-expresses myxoma SERP-1 as a secreted glycoprotein has been described elsewhere (Macen et al. 1993 Virology 195:348–363), and the procedures and methodologies employed in Macen et al. are herein incorporated by reference. To purify the expressed and secreted protein, 24 roller bottles ($3\times10^8$ cells per bottle) of BGMK cells were infected with VV-S1 or control virus that does not express SERP-1 (VV-601) at a multiplicity of 1–3 pfu/cell, adsorbed with Dulbecco's modified Eagles medium without serum. After 24 hours at 37 C., the decanted medium was clarified by centrifugation and the secreted proteins were dialyzed against 25 mM Tris, pH 8 and concentrated with an Amicon Centriprep-10 apparatus. The proteins from the VV-S1 or VV-601 Infected cells were then fractionated by FPLC, first by Mono-Q exchange column chromatography (Pharmacia) and then by Superdex-75 column chromatography (Pharmacia). The resulting protein samples were analyzed by SDS-PAGE and the proteins visualized by silver staining of the gel. FIG. 1, Lane 3.

FIG. 1, Lane 1 is vaccinia vector control proteins (after Mono Q column). Lane 2 is semi-purified SERP-1 (after Mono Q column). Lane 3 is purified SERP-1 (after Superdex column).

EXAMPLE 2

Infusion of SERP-1 at the Site of Angioplasty Induced Endothelial Denudation New Zealand white rabbits were fed a 2% cholesterol in 10% peanut oil diet for two weeks prior to intervention and four days per week thereafter. A 3–3.5 mm angioplasty balloon catheter was introduced via femoral cut down in rabbits anesthetized with intramuscular lanesthetic (premedication: 40 mg/kg ketalean, anesthetic: 8 mg/kg xylazene, and 0.5 mg/kg Acepromazine) and advanced to the distal abdominal aorta under fluoroscopic control.

During the angioplasty procedure, the balloon was inflated to a final pressure of 8 bars for two minutes and used to denude the endothelial layer of the entire aorta, then deflated. Immediately after balloon induced trauma, 10 ml of increasing concentrations of SERP-1 diluted in saline was infused onto sites of prior balloon mediated intimal damage in the distal abdominal aorta only. Infusions were introduced via a Wolinsky perfusion balloon catheter, a porous catheter that infuses agents locally into the intimal and medial layers of the arterial wall (Stadius et al., Am Heart J 126:47–56).

A total of fourteen rabbits were used in this study. Each of three rabbits in a first experimental group was administered 300 pg of semi-purified SERP-1, while each of three rabbits in a second experimental group was administered 30 pg of semi-purified SERP-1. Each of three rabbits in a third experimental group was administered 3 ng of SERP-1. The similarly purified vaccinia vector proteins were also infused onto sites of prior balloon mediated intimal damage in five separate control groups. The vector control protein dosages used for control experiments were equivalent to the vaccinia proteins in the semi-purified SERP-1 experiments.

EXAMPLE 3

Figure 2A:
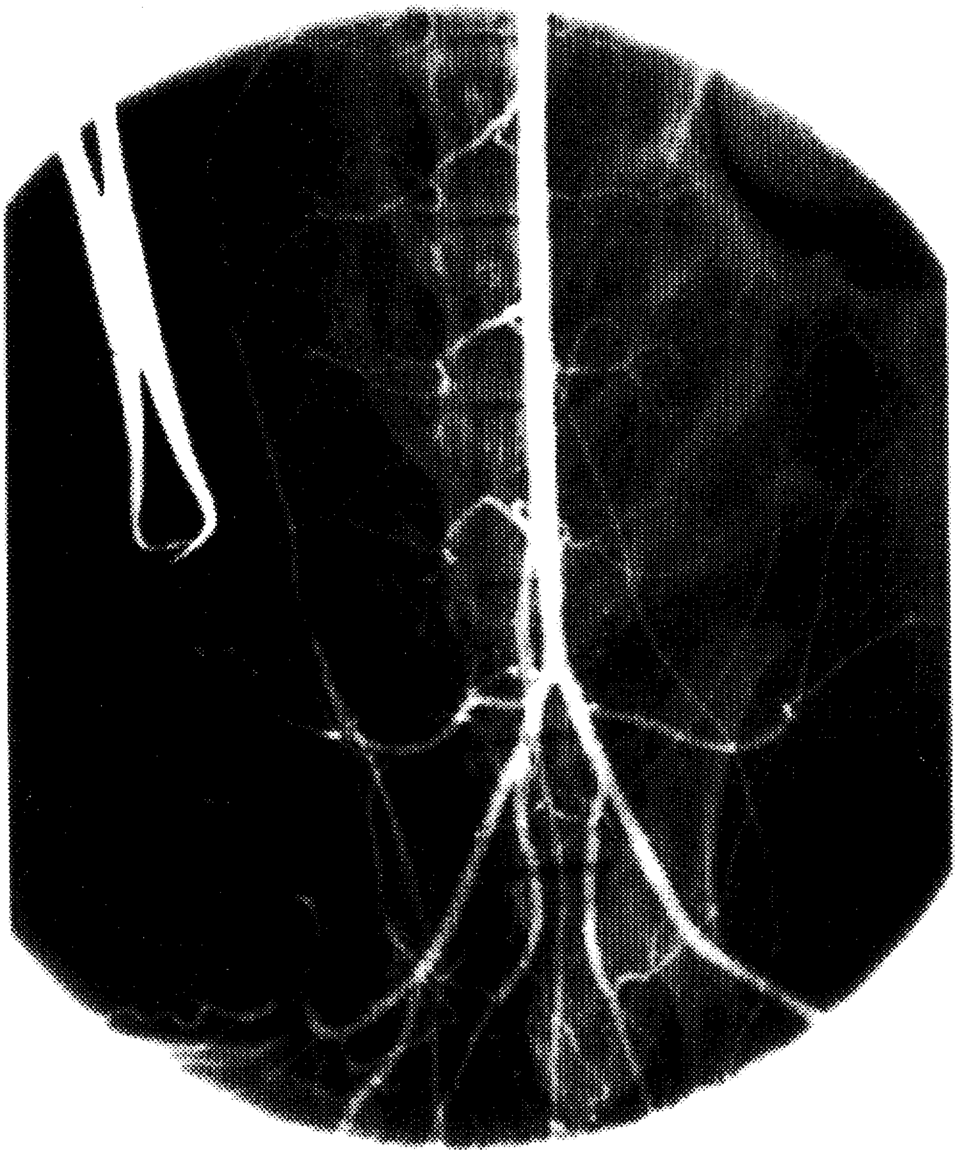
FIG. 2 shows two contrast angiograms taken four weeks after angioplasty. Panel A is an angiogram of an animal infused with the vaccinia vector control at the site of angioplastic injury. Panel B is an angiogram of an animal infused with semi-purified SERP-1 at the site of angioplastic injury.
Figure 2B:
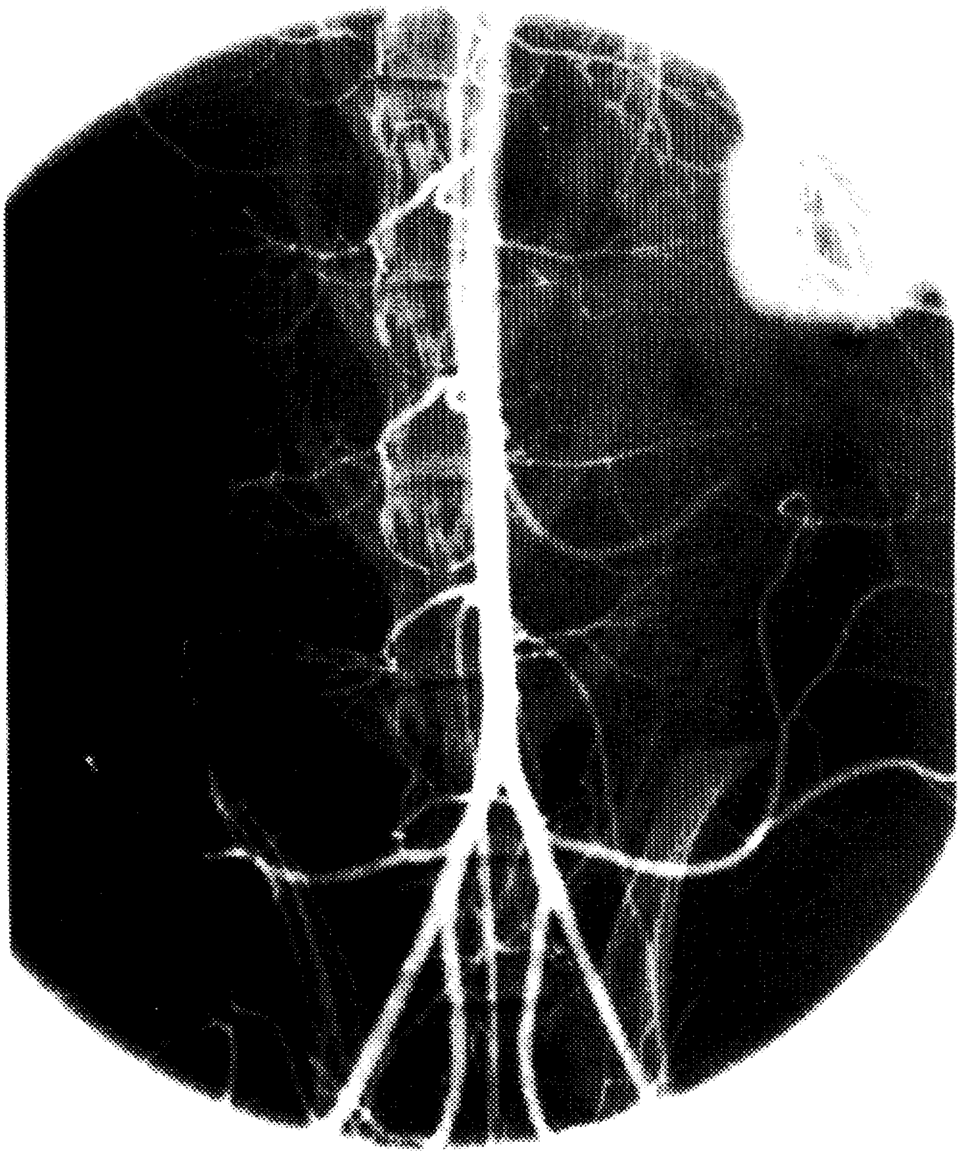

Analysis of SERP-1 Treated and Control Treated Aortas by Contrast Angiography Four weeks after angioplasty and either semi-purified SERP-1 or vaccinia control protein infusions, rabbits were examined for intimal proliferation and atherosclerotic plaque development by contrast angiography. Contrast angiography was performed by intra-arterial injection of standard contrast agents (e.g., Isovue). Angiography was recorded before and after angioplasty and at four weeks follow up, just prior to sacrifice. FIG. 2 shows two angiograms taken four weeks after angioplasty. Decreased stenosis at the site of SERP-1 infusion is visible in Panel B of FIG. 2.

Contrast angiography demonstrated virtually no change in the luminal diameter of the abdominal aorta after semi-purified SERP-1 infusion. Abdominal aorta diameters were measured by electronic calibrator. Abdominal aorta had a baseline luminal diameter of 4.05 mm. Four weeks after angioplasty and SERP-1 infusion, the luminal diameter was measured at 4.03 mm, p=0.9169, NS. In contrast, there was a measurable decrease in the abdominal aorta lumen diameter on contrast angiography four weeks after vaccinia vector control protein infusion. In the vaccinia vector control animals, abdominal aorta lumen had a baseline diameter of 4.28 mm. Four weeks later, the aorta lumen had a diameter of 3.496, p<0.0953. This difference is consistent with the histological findings of decreased atherosclerotic plaque development after SERP-1 infusion. There was no detectable increase in the lumen diameter immediately after balloon angioplasty and SERP-1 infusion. There was no difference in the incidence of visible associated complications between SERP-1 infusions or control infusions, i.e., dissection, thrombosis, hemorrhage, disseminated allergic or immune reaction and spasm.

EXAMPLE 4

Direct Visual Examination and Histological Analysis of Semi-Purified SERP-1 Treated and Control Treated Aortas Four weeks after semi-purified SERP-1 or control infusion, rabbits were sacrificed by Euthanyl injection. All surgical procedures and sacrifice of rabbits were performed according to the guidelines of the Animal Welfare Committee, University of Alberta and Canadian National Guidelines. After sacrifice, abdominal and thoracic aortas were immediately harvested for visual inspection and histological analysis of intimal surfaces.

Figure 3:
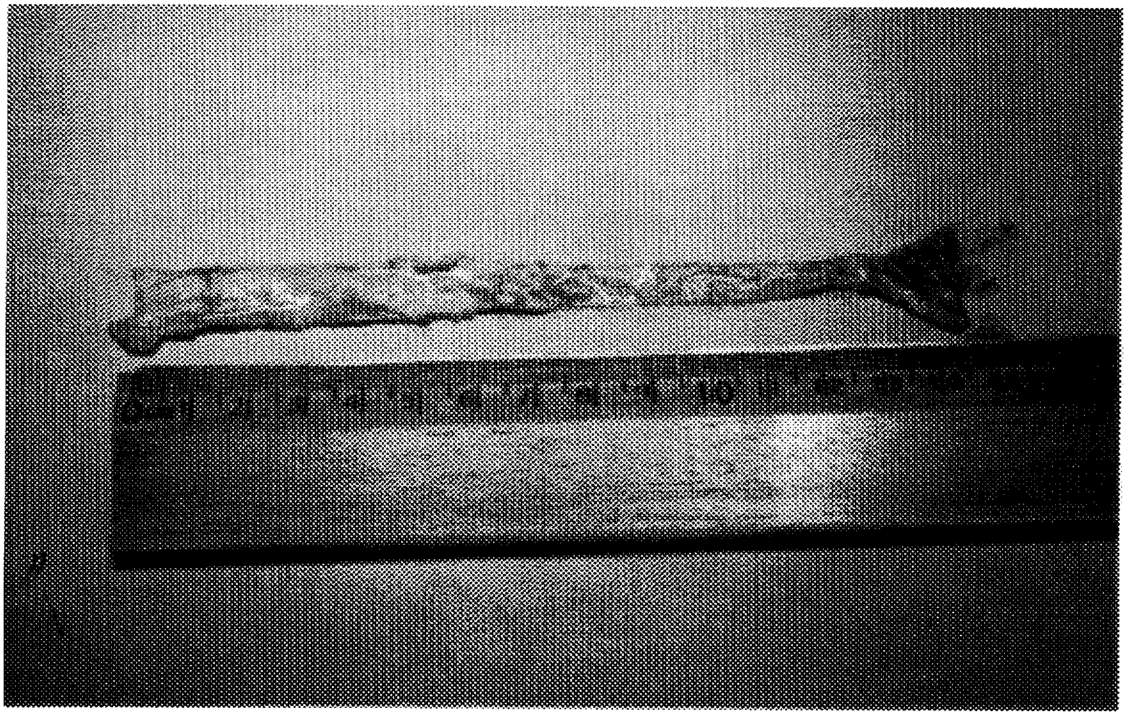
FIG. 3 is a photograph of the entire aorta from a rabbit which was administered 300 pg semi-purified SERP-1 and which aorta was removed immediately after sacrifice. Areas of balloon mediated intimal injury and SERP-1 infusion are indicated.

As seen in FIG. 3, atheromatous buildup is readily visible throughout the aorta. Also visible is a marked reduction in raised plaque at the area of semi-purified SERP-1 infusion (FIG. 3). In contrast, the thoracic aorta above the site of semi-purified SERP-1 infusion and the iliac bifurcation below the site of infusion have visible areas of raised fatty plaque (FIG. 3).

Comparison of aortas removed from experimental animals with those removed from control animals revealed a significant decrease in plaque development at sites of prior intimal damage In the abdominal aorta after semi-purified SERP-1 infusion but not after saline or vaccinia vector infusion. Plaque development was not altered in other areas of the aorta; the amount of plaque observed on visual examination of the thoracic aorta above the site of infusion and in the iliac arteries below the infusion site either after semi-purified SERP-1 infusion or control infusion was similar.

For histological analysis, sections were taken from the thoracic aorta above the site of balloon angioplasty, the iliac bifurcation below the site of angioplasty, and the abdominal aorta at the site of angioplasty in both experimental and control animals. Specimens of aorta were fixed in neutral buffered foramen and stained with hematoxylin and eosin as follows. Specimens were embedded in paraffin and cut in 3–4 micron sections. The sections were treated with a graded series of alcohol and xylem washes and then stained with hematoxylin and eosin.

Plaque thickness and area were measured by morphometric analysis using a Jandell scientific drawing tube and MAC-OMA software as has been previously described (21–22 PreII). The intimal area was drawn for subsequent measurement using a drawing tube attachment with a Nikon Labophot II microscope. Intimal thickness was also assessed by an ocular micrometer attached to the microscope. The grossly visible decrease in plaque development after semi-purified SERP-1 infusion was confirmed by histological examination (FIG. 4*a*).

A 14 fold decrease in plaque area and a 28 fold decrease in plaque thickness was detected after semi-purified SERP-1 infusion in the abdominal aorta (FIG. 5 and Table 1). Mean atherosclerotic plaque thickness measured at the site of balloon angioplasty in the abdominal aorta was 94±33 microns after semi-purified SERP-1 infusion and 436±100 microns after vaccinia vector control infusion (p<0.0017). Mean plaque area in the abdominal aorta was 0.037±0.016 mm2 after SERP-1 infusion and 0.516±0.163 after vaccinia control infusion (p<0.0017).

There was no significant decrease in the plaque development above and below the sites of semi-purified SERP-1 infusion indicating that the SERP-1 effect was a local effect only. Semi-purified SERP-1 produced a decrease in subsequent plaque growth that was limited to the site of infusion. In the thoracic aorta sections, plaque thickness was measured at a mean value of 146±54 microns after SERP-1 infusion and 606±131 microns after saline control infusion (p=0.1392, NS); plaque area was 0.695±0.199 $mm^2$ after SERP-1 infusion and 1.265±0.391 $mm^2$ after saline control infusion (p=0.1392, NS). Similar values were recorded by morphometric analysis of the iliac arteries, again indicating that the SERP-1 effect was quite localized with no evidence of distal washout of the infused SERP-1 protein (FIG. 5 and Table 1).

Figure 4A:
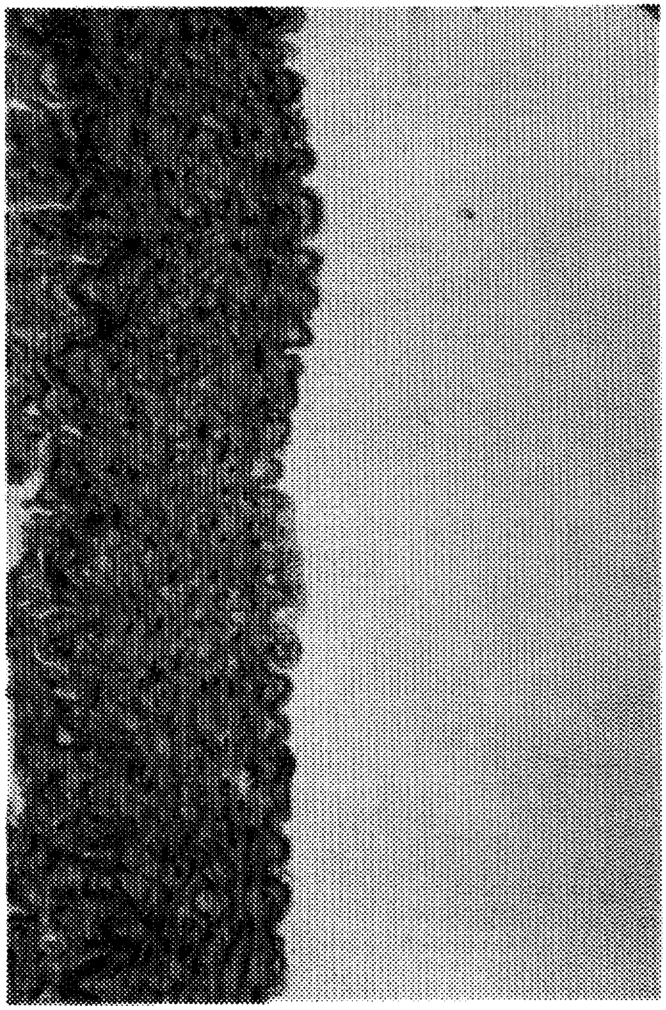
FIG. 4*a* shows a hematoxylin and eosin stained section of a semi-purified SERP-1 treated rabbit abdominal aorta.
Figure 4B:
FIG. 4*b* shows a hematoxylin and eosin stained section of a vaccinia vector control protein treated rabbit abdominal aorta.
Figure 4C:
FIG. 4*c* shows a hematoxylin and eosin stained section of a saline control treated rabbit abdominal aorta.
Figure 5B:
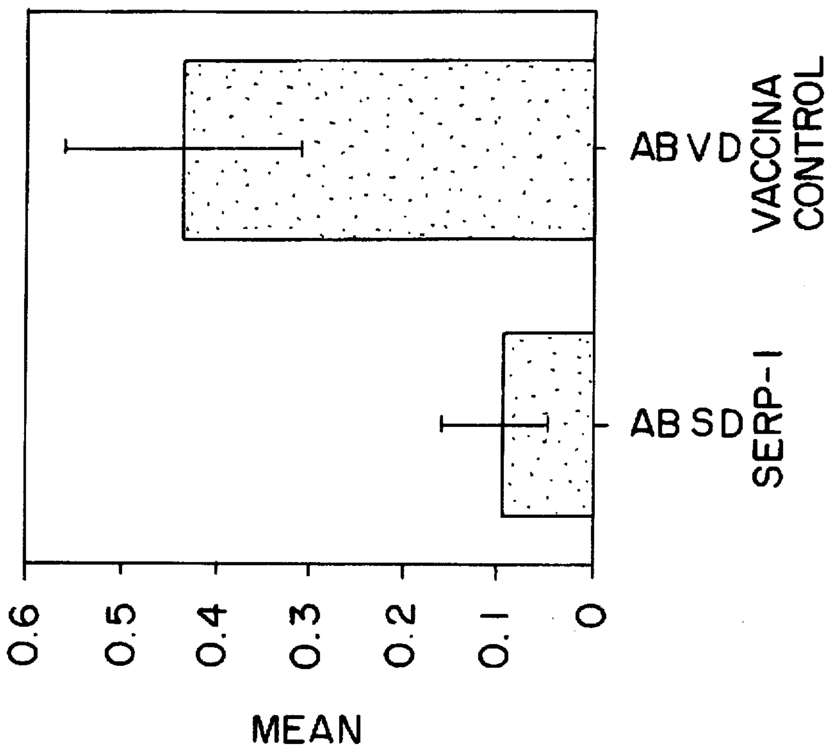
FIG. 5*b* shows abdominal aorta plaque thickness at the site of prior angioplasty, after semi-purified SERP-1 and vaccinia vector control protein infusion.
Figure 5A:
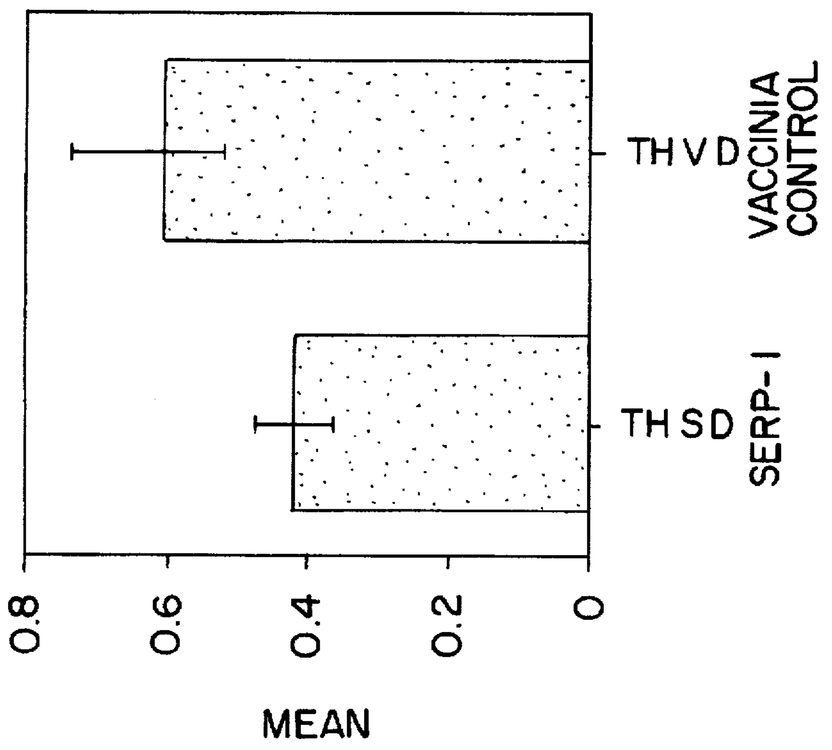
FIG. 5*a* shows thoracic aorta intimal thickness after semi-purified SERP-1 and vaccinia vector control protein infusion.
Figure 5D:
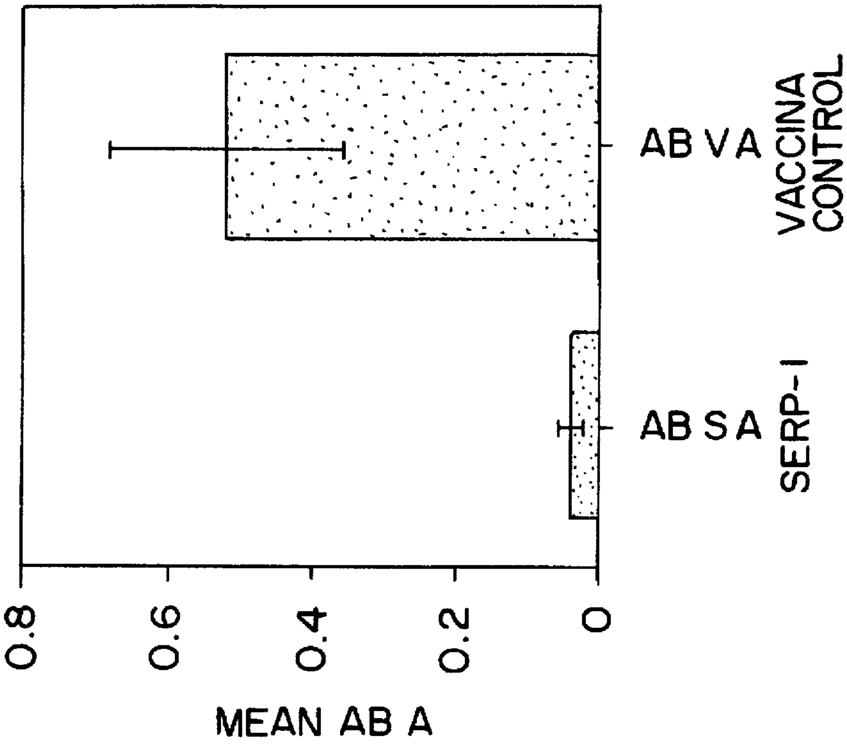
FIG. 5*d* shows abdominal aorta plaque area four weeks post angioplasty.
Figure 5C:
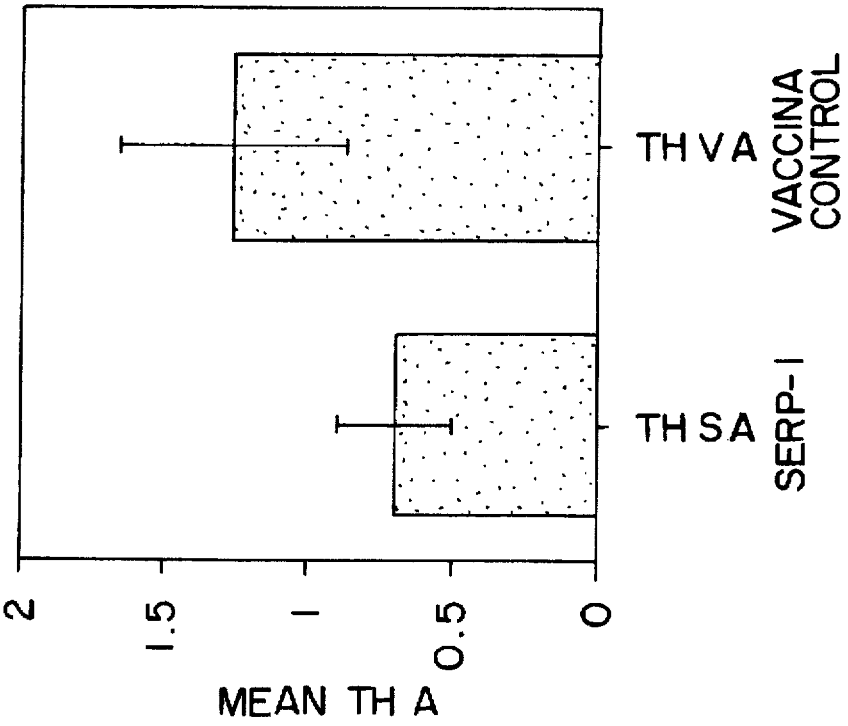
FIG. 5*c* shows thoracic aorta plaque area after semi-purified SERP-1 and vaccinia vector control protein infusion.
Figure 6B:
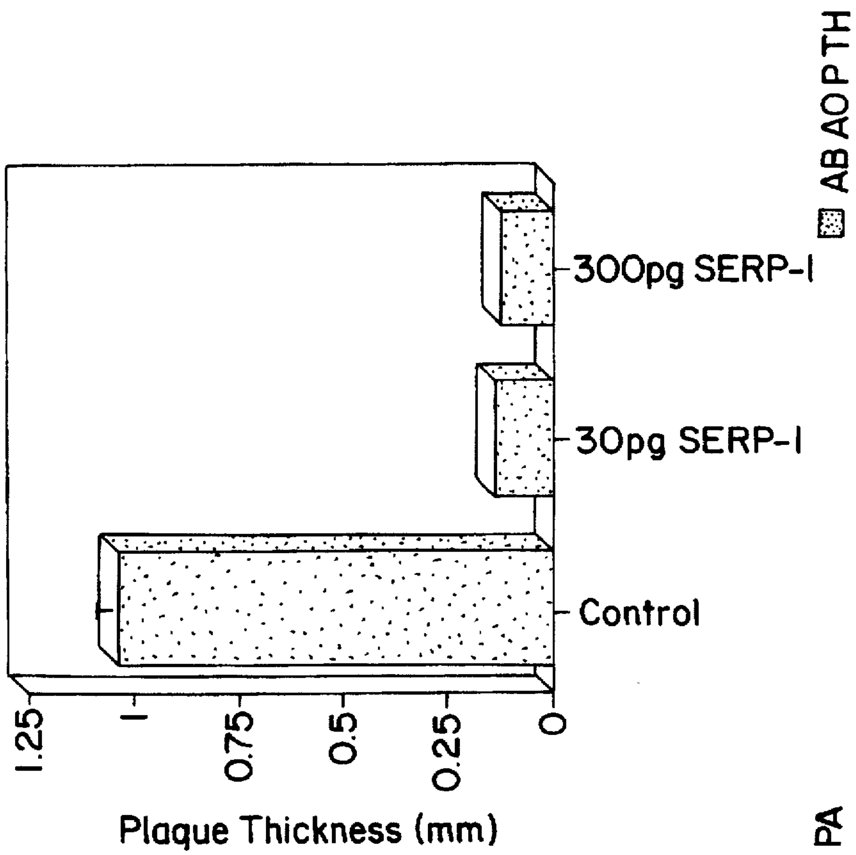
FIG. 6*b* shows the plaque thickness of primary infusion sites [abdominal aortas] treated with purified SERP-1 or control saline.
Figure 6A:
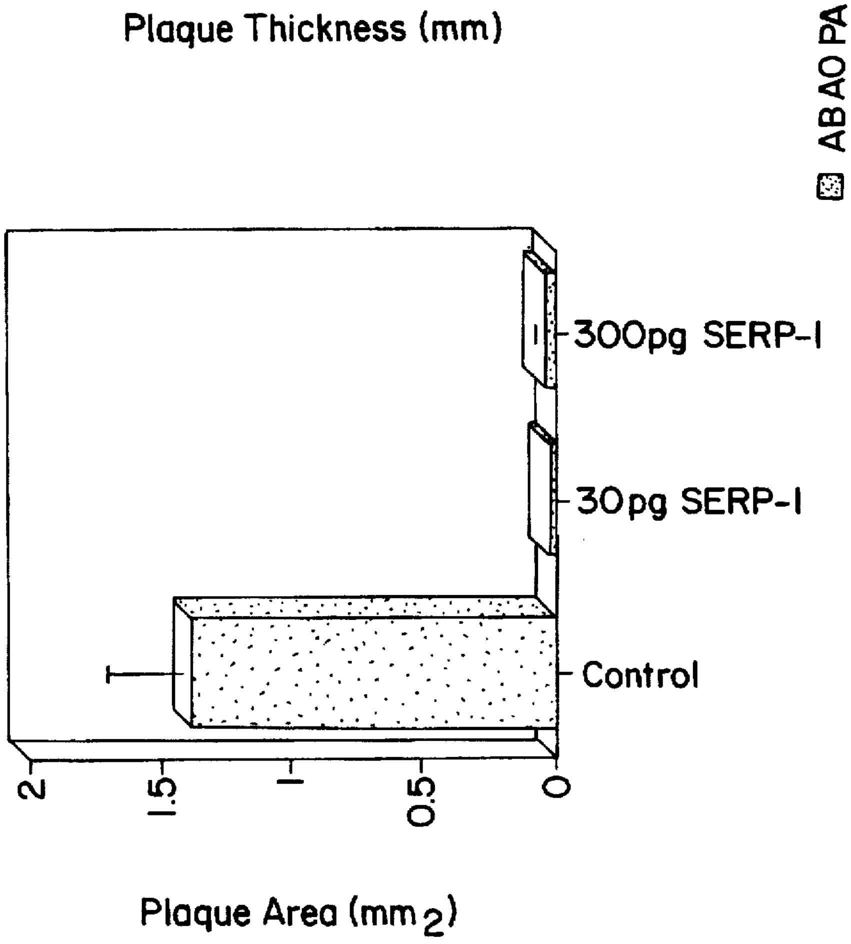
FIG. 6*a* shows the plaque area of primary infusion sites [abdominal aortas] treated with purified SERP-1 or control saline.
Figure 6D:
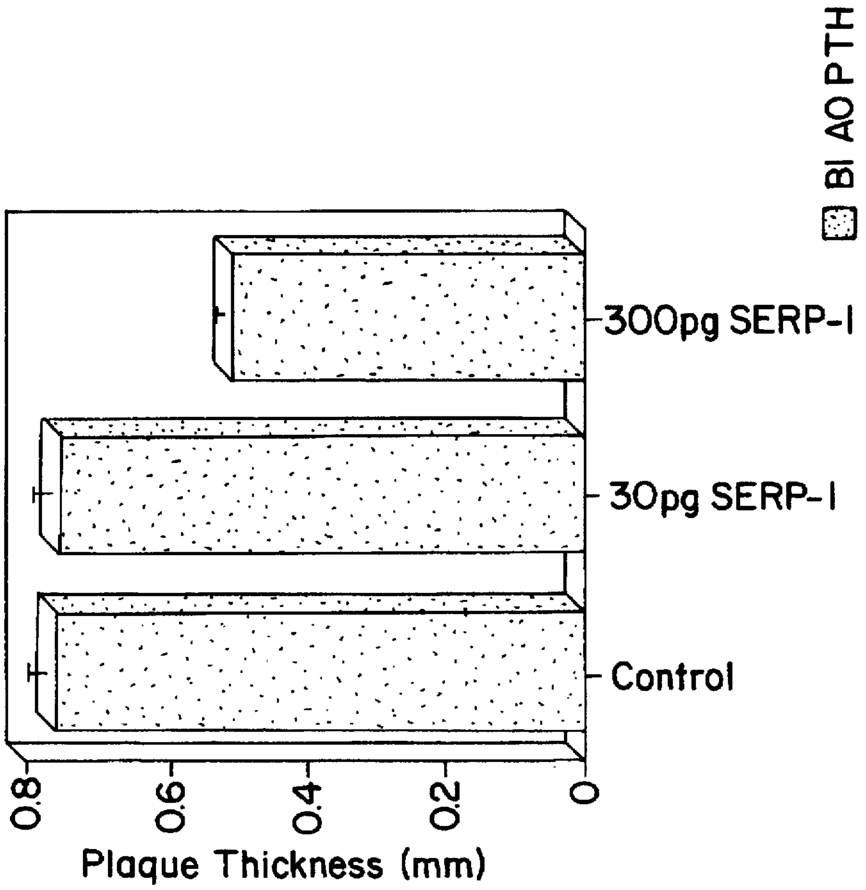
FIG. 6*d* shows plaque thickness of secondary non-infused sites [iliac arteries] treated with purified SERP-1 or control saline.
Figure 6C:
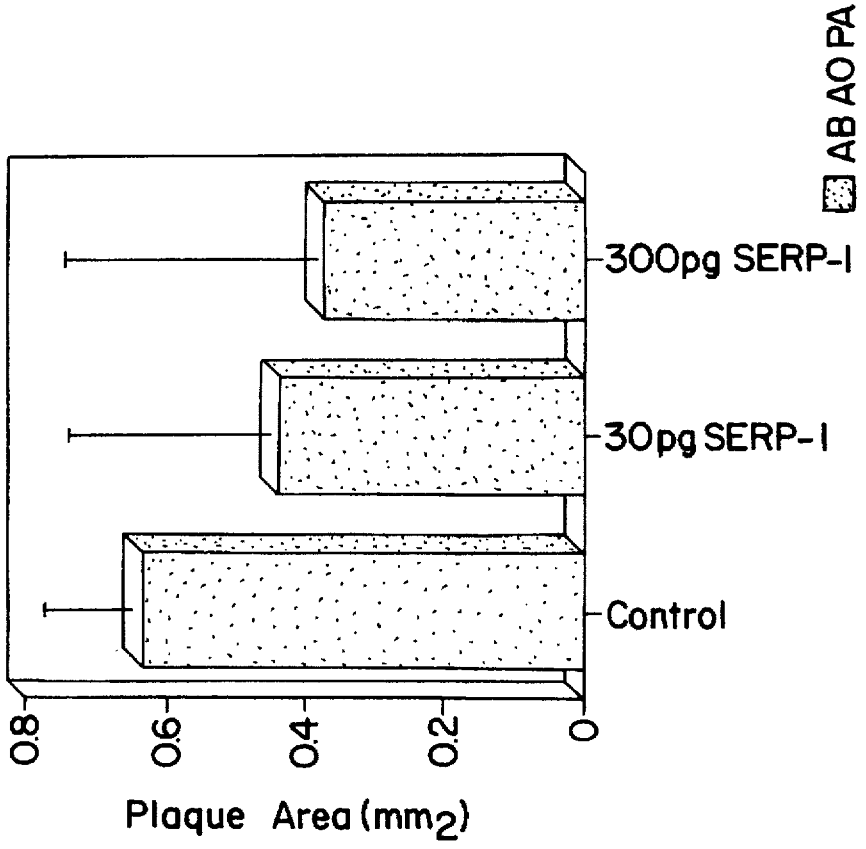
FIG. 6*c* shows plaque areas of secondary non-infused sites [iliac arteries] treated with purified SERP-1 or control saline.

Atherosclerotic plaque detectable in semi-purified SERP-1 treated rabbits at sites on infusion was generally a thin layer of fatty intimal hyperplasia (FIG. 4*a*). In contrast, plaque detectable after infusion of saline or the vaccinia vector control (FIG. 4*b*) was often complex extending over large areas of the intima with both fatty and fibrous cellular proliferation. In some cases a fibrous cap was visible (FIG. 4*c*). At sites above and below infusion or in the control rabbits infused with the vaccinia vector control or saline, there was often abundant fatty and fibrous plaque, often moderately complex.

The greatest anti-restenosis effect was seen with infusion of 300 pg to 3 ng of semi-purified SERP-1. Dose concentrations of 30 pg of semi-purified SERP-1 provided much less pronounced inhibition of intimal proliferation and atherosclerotic plaque development.

TABLE 1

| | Intimal Thickness (mm) | | | Intimal Area ($mm^2$) | | |
|---|---|---|---|---|---|---|
| Infusion | Thoracic | Abdominal | Iliac | Thoracic | Abdominal | Iliac |
| SERP-1 | 0.416 ± .054 | 0.094 ± .033 | 0.223 ± .065 | 0.695 ± .199 | 0.037 ± .016 | 0.347 ± .123 |
| Vaccinia Vector | 0.606 ± .131 | 0.436 ± .100 | 0.432 ± .125 | 1.265 ± .391 | 0.516 ± .163 | 0.568 ± .236 |
| Saline | 0.625 ± .145 | 0.835 ± .345 | 0.265 ± .265 | 1.394 ± .183 | 1.049 ± .429 | 0.152 ± .137 |

EXAMPLE 5

Fully Purified SERP-1 Protein Retains Full Biological Activity

In FIGS. 6*a*, 6*b*, 6*c* and 6*d* is shown data for twelve rabbits treated with fully purified SERP-1 or control saline as described in Examples 2–4. The data for plaque area (FIG. 6*a*) and plaque thickness (FIG. 6*b*) at the primary site of infusion of purified SERP-1 show even greater efficacy than for the semi-purified SERP-1.

A seventy three fold decrease in plaque area and an eight fold decrease in plaque thickness was observed for both SERP-1 concentrations tested over the D saline controls. Mean plaque thickness measured at the site of balloon angioplasty in the abdominal aorta was 134±79 microns after purified SERP-1 infusion and 1,035±107 microns after control saline infusion [p<0001]. Mean plaque area in the abdominal aorta was 0.019±0.011 $mm^2$ after SERP-1 infusion and 1.39±0.308 $mm^2$ after saline infusion [p<004].

In the case of secondary non-infused sites (FIGS. 6*c* and 6*d*), a modest but not statistically significant reduction at the 300 pg level of purified SERP-1 was noted. The purified SERP-1 (See FIG. 1, Lane 3) was even more potent on a molar basis than the semi-purified (FIG. 1, Lane 2) in reducing restenosis following balloon angioplasty.

What is claimed:

1. A method of treating primary or recurrent plaque development in an artery which comprises administering a therapeutically effective amount of SERP-1 directly onto an atheromatous site.

2. A method of treating primary plaque development in an artery which comprises delivering a therapeutically effective amount of SERP-1 the arterial endothelium.

3. The method of claim 2 wherein the SERP-1 is delivered by peripheral intravenous or intra-arterial infusion.

4. The method of claim 1 wherein the SERP-1 is delivered intra-arterially by a weeping balloon type catheter.

5. A method of treating restenosis resulting after an arterial recanalization intervention procedure which comprises administering a therapeutically effective amount of SERP-1 at the site of recanalization.

6. The method of claim 5 wherein the arterial recannalization intervention procedure is balloon angioplasty.

7. The method of claim 5 wherein the arterial recannalization intervention procedure is laser angioplasty.

8. The method of claim 5 wherein the arterial recannalization intervention procedure is stent implantation.

9. The method of claim 5 wherein the arterial recannalization intervention procedure is atherectomy.

10. The method of claim 5 wherein the arterial recannalization intervention procedure is vein or arterial graft.

11. The method of claim 5, wherein the arterial recannalization intervention procedure is coronary bypass surgery.

12. The method of any one of claims 1–5 wherein SERP-1 comprises an amino acid other than cysteine at position 244.

13. The method of any one of claims 1–5 wherein SERP-1 comprises an amino acid other than arginine at position 319.

14. The method of any one of claims 1–5 wherein SERP-1 comprises an amino acid other than asparagine at position 320.

15. The method of any one of claims 1–5 wherein SERP-1 comprises an amino acid other than arginine at position 319 and an amino acid other than asparagine at position 320.

16. A method of treating urethral or uretal stricture which comprises administering a therapeutically effective amount of SERP-1 to the lumenal layers of the urethra and/or uterers.

17. A pharmaceutical composition comprising SERP-1 admixed with a pharmaceutically acceptable carrier.

18. A pharmaceutical composition of claim 17 wherein said SERP-1 comprises an amino acid other than cysteine at position 244.

19. A pharmaceutical composition of claim 17 wherein said SERP-1 comprises an alanine residue at position 244.

20. A pharmaceutical composition of claim 17 wherein said SERP-1 comprises an amino acid other than arginine at position 319.

21. A pharmaceutical composition comprising SERP-1 having an amino acid other than asparagine at position 320.

22. A pharmaceutical composition comprising SERP-1 having an amino acid other than arginine at position 319 and asparagine at position 320.

23. A method of treating inflammation following arterial intimal injury which comprises blocking the action of SERP-1 cognate serine proteases by administering a therapeutically effective amount of SERP-1.

24. A method of treating inflammation following arterial intimal injury comprising administering a therapeutically effective amount of SERP-1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1138 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1110

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | AAG | TAT | CTG | GTC | CTC | GTC | TTA | TGT | TTA | ACG | TCG | TGC | GCG | TGT | CGA | 48 |
| Met | Lys | Tyr | Leu | Val | Leu | Val | Leu | Cys | Leu | Thr | Ser | Cys | Ala | Cys | Arg | |
| 1 | | | | 5 | | | | | 10 | | | | | 15 | | |
| GAT | ATC | GGA | CTA | TGG | ACG | TTC | CGA | TAC | GTC | TAC | AAC | GAA | AGC | GAC | AAC | 96 |
| Asp | Ile | Gly | Leu | Trp | Thr | Phe | Arg | Tyr | Val | Tyr | Asn | Glu | Ser | Asp | Asn | |
| | | | | 20 | | | | | 25 | | | | | 30 | | |
| GTC | GTG | TTC | TCA | CCG | TAC | GGC | TTG | ACC | TCC | GCG | TTG | TCC | GTG | TTA | CGG | 144 |
| Val | Val | Phe | Ser | Pro | Tyr | Gly | Leu | Thr | Ser | Ala | Leu | Ser | Val | Leu | Arg | |
| | | 35 | | | | | 40 | | | | | 45 | | | | |
| ATC | GCG | GCG | GGC | GGT | AAC | ACG | AAA | CGA | GAA | ATA | GAC | GTC | CCC | GAA | TCC | 192 |
| Ile | Ala | Ala | Gly | Gly | Asn | Thr | Lys | Arg | Glu | Ile | Asp | Val | Pro | Glu | Ser | |
| | 50 | | | | | 55 | | | | | 60 | | | | | |
| GTC | GTG | GAG | GAC | TCC | GAC | GCC | TTT | CTC | GCG | TTA | CGG | GAG | TTG | TTC | GTA | 240 |
| Val | Val | Glu | Asp | Ser | Asp | Ala | Phe | Leu | Ala | Leu | Arg | Glu | Leu | Phe | Val | |
| 65 | | | | | 70 | | | | | 75 | | | | | 80 | |
| GAC | GCA | TCC | GTT | CCG | TTA | CGT | CCC | GAG | TTT | ACG | GCG | GAG | TTC | TCC | TCG | 288 |
| Asp | Ala | Ser | Val | Pro | Leu | Arg | Pro | Glu | Phe | Thr | Ala | Glu | Phe | Ser | Ser | |
| | | | | 85 | | | | | 90 | | | | | 95 | | |
| CGA | TTC | AAT | ACC | TCC | GTG | CAA | CGC | GTG | ACG | TTT | AAC | TCG | GAG | AAC | GTC | 336 |
| Arg | Phe | Asn | Thr | Ser | Val | Gln | Arg | Val | Thr | Phe | Asn | Ser | Glu | Asn | Val | |
| | | | 100 | | | | | 105 | | | | | 110 | | | |
| AAA | GAC | GTC | ATT | AAC | TCG | TAC | GTT | AAG | GAT | AAG | ACG | GGA | GGA | GAC | GTC | 384 |
| Lys | Asp | Val | Ile | Asn | Ser | Tyr | Val | Lys | Asp | Lys | Thr | Gly | Gly | Asp | Val | |
| | | 115 | | | | | 120 | | | | | 125 | | | | |
| CCA | CGC | GTA | TTG | GAC | GCC | TCC | CTA | GAC | CGA | GAT | ACT | AAA | ATG | CTG | CTA | 432 |
| Pro | Arg | Val | Leu | Asp | Ala | Ser | Leu | Asp | Arg | Asp | Thr | Lys | Met | Leu | Leu | |
| | 130 | | | | | 135 | | | | | 140 | | | | | |
| TTG | AGC | TCC | GTT | CGT | ATG | AAG | ACG | AGC | TGG | AGA | CAC | GTA | TTC | GAC | CCT | 480 |
| Leu | Ser | Ser | Val | Arg | Met | Lys | Thr | Ser | Trp | Arg | His | Val | Phe | Asp | Pro | |

-continued 145 150 155 160

TCG TTC ACG ACG GAT CAA CCT TTT TAT TCC GGA AAC GTC ACA TAC AAG 528
Ser Phe Thr Thr Asp Gln Pro Phe Tyr Ser Gly Asn Val Thr Tyr Lys
165 170 175

GTA CGT ATG ATG AAT AAA ATA GAT ACG TTG AAA ACG GAG ACG TTT ACG 576
Val Arg Met Met Asn Lys Ile Asp Thr Leu Lys Thr Glu Thr Phe Thr
180 185 190

CTT AGA AAC GTG GGA TAC TCC GTA ACG GAA CTG CCG TAT AAA CGG CGT 624
Leu Arg Asn Val Gly Tyr Ser Val Thr Glu Leu Pro Tyr Lys Arg Arg
195 200 205

CAA ACG GCC ATG TTG CTC GTC GTT CCG GAC GAC TTG GGA GAG ATC GTG 672
Gln Thr Ala Met Leu Leu Val Val Pro Asp Asp Leu Gly Glu Ile Val
210 215 220

CGG GCC CTC GAT CTT TCT CTA GTA CGC TTC TGG ATA CGC AAC ATG AGG 720
Arg Ala Leu Asp Leu Ser Leu Val Arg Phe Trp Ile Arg Asn Met Arg
225 230 235 240

AAA GAC GTG TGT CAG GTG GTA ATG CCC AAG TTC TCC GTC GAA TCG GTC 768
Lys Asp Val Cys Gln Val Val Met Pro Lys Phe Ser Val Glu Ser Val
245 250 255

CTG GAT CTG AGG GAC GCC CTC CAG AGA CTG GGG GTG CGA GAC GCG TTC 816
Leu Asp Leu Arg Asp Ala Leu Gln Arg Leu Gly Val Arg Asp Ala Phe
260 265 270

GAT CCA TCC CGG GCG GAC TTC GGT CAG GCG TCC CCG TCG AAC GAT CTA 864
Asp Pro Ser Arg Ala Asp Phe Gly Gln Ala Ser Pro Ser Asn Asp Leu
275 280 285

TAC GTC ACG AAG GTG TTA CAG ACG TCC AAG ATA GAG GCG GAC GAA CGG 912
Tyr Val Thr Lys Val Leu Gln Thr Ser Lys Ile Glu Ala Asp Glu Arg
290 295 300

GGA ACG ACG GCG TCG AGC GAC ACA GCC ATC ACC CTC ATC CCC AGG AAC 960
Gly Thr Thr Ala Ser Ser Asp Thr Ala Ile Thr Leu Ile Pro Arg Asn
305 310 315 320

GCC CTC ACG GCG ATC GTG GCG AAC AAA CCG TTT ATG TTT CTC ATC TAT 1008
Ala Leu Thr Ala Ile Val Ala Asn Lys Pro Phe Met Phe Leu Ile Tyr
325 330 335

CAC AAG CCT ACA ACG ACC GTG TTG TTT ATG GGA ACG ATA ACA AAG GGT 1056
His Lys Pro Thr Thr Thr Val Leu Phe Met Gly Thr Ile Thr Lys Gly
340 345 350

GAA AAA GTA ATA TAC GAT ACG GAG GGT CGA GAT GAT GTC GTA TCC TCT 1104
Glu Lys Val Ile Tyr Asp Thr Glu Gly Arg Asp Asp Val Val Ser Ser
355 360 365

GTA TAA ACTCTTTTTG AAGGGTAAAC TATGCGAC 1138
Val *
370

( 2 ) INFORMATION FOR SEQ ID NO:2:

( i ) SEQUENCE CHARACTERISTICS:
( A ) LENGTH: 369 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Lys Tyr Leu Val Leu Val Leu Cys Leu Thr Ser Cys Ala Cys Arg
1 5 10 15

Asp Ile Gly Leu Trp Thr Phe Arg Tyr Val Tyr Asn Glu Ser Asp Asn
20 25 30

Val Val Phe Ser Pro Tyr Gly Leu Thr Ser Ala Leu Ser Val Leu Arg
35 40 45

Ile Ala Ala Gly Gly Asn Thr Lys Arg Glu Ile Asp Val Pro Glu Ser

-continued

| | | | | | | | | | | | | | | | |
|---|---|---|---|---|---|---|---|---|---|---|---|---|---|---|---|
| | 50 | | | | | 55 | | | | | 60 | | | | |
| Val | Val | Glu | Asp | Ser | Asp | Ala | Phe | Leu | Ala | Leu | Arg | Glu | Leu | Phe | Val |
| 65 | | | | | 70 | | | | | 75 | | | | | 80 |
| Asp | Ala | Ser | Val | Pro | Leu | Arg | Pro | Glu | Phe | Thr | Ala | Glu | Phe | Ser | Ser |
| | | | | 85 | | | | | 90 | | | | | 95 | |
| Arg | Phe | Asn | Thr | Ser | Val | Gln | Arg | Val | Thr | Phe | Asn | Ser | Glu | Asn | Val |
| | | | 100 | | | | | 105 | | | | | 110 | | |
| Lys | Asp | Val | Ile | Asn | Ser | Tyr | Val | Lys | Asp | Lys | Thr | Gly | Gly | Asp | Val |
| | | 115 | | | | | 120 | | | | | 125 | | | |
| Pro | Arg | Val | Leu | Asp | Ala | Ser | Leu | Asp | Arg | Asp | Thr | Lys | Met | Leu | Leu |
| | 130 | | | | | 135 | | | | | 140 | | | | |
| Leu | Ser | Ser | Val | Arg | Met | Lys | Thr | Ser | Trp | Arg | His | Val | Phe | Asp | Pro |
| 145 | | | | | 150 | | | | | 155 | | | | | 160 |
| Ser | Phe | Thr | Thr | Asp | Gln | Pro | Phe | Tyr | Ser | Gly | Asn | Val | Thr | Tyr | Lys |
| | | | | 165 | | | | | 170 | | | | | 175 | |
| Val | Arg | Met | Met | Asn | Lys | Ile | Asp | Thr | Leu | Lys | Thr | Glu | Thr | Phe | Thr |
| | | | 180 | | | | | 185 | | | | | 190 | | |
| Leu | Arg | Asn | Val | Gly | Tyr | Ser | Val | Thr | Glu | Leu | Pro | Tyr | Lys | Arg | Arg |
| | | 195 | | | | | 200 | | | | | 205 | | | |
| Gln | Thr | Ala | Met | Leu | Leu | Val | Val | Pro | Asp | Asp | Leu | Gly | Glu | Ile | Val |
| | 210 | | | | | 215 | | | | | 220 | | | | |
| Arg | Ala | Leu | Asp | Leu | Ser | Leu | Val | Arg | Phe | Trp | Ile | Arg | Asn | Met | Arg |
| 225 | | | | | 230 | | | | | 235 | | | | | 240 |
| Lys | Asp | Val | Cys | Gln | Val | Val | Met | Pro | Lys | Phe | Ser | Val | Glu | Ser | Val |
| | | | | 245 | | | | | 250 | | | | | 255 | |
| Leu | Asp | Leu | Arg | Asp | Ala | Leu | Gln | Arg | Leu | Gly | Val | Arg | Asp | Ala | Phe |
| | | | 260 | | | | | 265 | | | | | 270 | | |
| Asp | Pro | Ser | Arg | Ala | Asp | Phe | Gly | Gln | Ala | Ser | Pro | Ser | Asn | Asp | Leu |
| | | 275 | | | | | 280 | | | | | 285 | | | |
| Tyr | Val | Thr | Lys | Val | Leu | Gln | Thr | Ser | Lys | Ile | Glu | Ala | Asp | Glu | Arg |
| | 290 | | | | | 295 | | | | | 300 | | | | |
| Gly | Thr | Thr | Ala | Ser | Ser | Asp | Thr | Ala | Ile | Thr | Leu | Ile | Pro | Arg | Asn |
| 305 | | | | | 310 | | | | | 315 | | | | | 320 |
| Ala | Leu | Thr | Ala | Ile | Val | Ala | Asn | Lys | Pro | Phe | Met | Phe | Leu | Ile | Tyr |
| | | | | 325 | | | | | 330 | | | | | 335 | |
| His | Lys | Pro | Thr | Thr | Thr | Val | Leu | Phe | Met | Gly | Thr | Ile | Thr | Lys | Gly |
| | | | 340 | | | | | 345 | | | | | 350 | | |
| Glu | Lys | Val | Ile | Tyr | Asp | Thr | Glu | Gly | Arg | Asp | Asp | Val | Val | Ser | Ser |
| | | 355 | | | | | 360 | | | | | 365 | | | |
| Val | * | | | | | | | | | | | | | | |
| | 370 | | | | | | | | | | | | | | |